US007052854B2

(12) United States Patent
Melker et al.

(10) Patent No.: US 7,052,854 B2
(45) Date of Patent: May 30, 2006

(54) APPLICATION OF NANOTECHNOLOGY AND SENSOR TECHNOLOGIES FOR EX-VIVO DIAGNOSTICS

(75) Inventors: Richard J. Melker, Gainesville, FL (US); Ronald L. Hayes, Gainesville, FL (US); Ka-Wang Kevin Wang, Gainesville, FL (US); Donn Michael Dennis, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 189 days.

(21) Appl. No.: 10/678,506

(22) Filed: Oct. 2, 2003

(65) Prior Publication Data
US 2006/0040318 A1    Feb. 23, 2006

Related U.S. Application Data

(63) Continuation-in-part of application No. 10/345,532, filed on Jan. 16, 2003, and a continuation-in-part of application No. 10/154,201, filed on May 22, 2002, and a continuation-in-part of application No. 10/274,829, filed on Oct. 21, 2002.

(60) Provisional application No. 60/292,962, filed on May 23, 2001.

(51) Int. Cl.
G01N 33/53    (2006.01)

(52) U.S. Cl. .............................. 435/7.1; 435/4; 435/6; 436/501; 436/535; 422/68.1; 422/82.01; 422/82.02; 422/98

(58) Field of Classification Search ................. 435/7.1, 435/6, 182, 4; 436/535, 501; 73/23.2, 24.06; 422/68.1, 82.01, 82.02, 98; 702/19, 22
See application file for complete search history.

(56) References Cited

U.S. PATENT DOCUMENTS

| | | |
|---|---|---|
| 3,567,029 A | 3/1971 | Quame |
| 3,608,546 A | 9/1971 | Shinn |
| 3,649,199 A | 3/1972 | Littlejohn |
| 3,792,272 A | 2/1974 | Harte et al. |
| 3,877,291 A | 4/1975 | Hoppesch et al. |
| 3,951,607 A | 4/1976 | Fraser |
| 3,955,926 A | 5/1976 | Fischer |
| 4,150,670 A | 4/1979 | Jewett et al. |
| 4,202,352 A | 5/1980 | Osborn |
| 4,215,409 A | 7/1980 | Strowe |
| 4,312,228 A | 1/1982 | Wohltjen |
| 4,314,564 A | 2/1982 | Albarda |
| 4,334,540 A | 6/1982 | Preti et al. |
| 4,346,584 A | 8/1982 | Boehringer |
| 4,349,626 A | 9/1982 | Labows et al. |
| 4,361,026 A | 11/1982 | Muller et al. |
| 4,399,686 A | 8/1983 | Kindlund et al. |
| 4,432,226 A | 2/1984 | Dempster |
| 4,456,014 A | 6/1984 | Buck et al. |
| 4,534,360 A | 8/1985 | Williams |
| 4,734,777 A | 3/1988 | Okino et al. |
| 4,735,777 A | 4/1988 | Mitsui et al. |
| 4,772,559 A | 9/1988 | Preti et al. |
| 4,796,639 A | 1/1989 | Snow et al. |
| 4,868,545 A | 9/1989 | Jones |
| 4,895,017 A | 1/1990 | Pyke et al. |
| 4,938,928 A | 7/1990 | Koda et al. |
| 4,992,244 A | 2/1991 | Grate |
| 5,003,985 A | 4/1991 | White et al. |
| 5,034,192 A | 7/1991 | Wrighton et al. |
| 5,042,501 A | 8/1991 | Kenny et al. |
| 5,060,506 A | 10/1991 | Douglas |
| 5,071,770 A | 12/1991 | Kolesar, Jr. |
| 5,081,871 A | 1/1992 | Glaser |
| 5,082,630 A | 1/1992 | Partin et al. |
| 5,094,235 A | 3/1992 | Westenskow et al. |
| 5,111,827 A | 5/1992 | Rantala |
| 5,137,692 A | 8/1992 | Fritz |
| 5,145,645 A | 9/1992 | Zakin et al. |
| 5,167,972 A | 12/1992 | Greenberg et al. |
| 5,179,027 A | 1/1993 | Fisher |
| 5,252,292 A | 10/1993 | Hirata et al. |
| 5,296,706 A | 3/1994 | Braig et al. |
| 5,303,575 A | 4/1994 | Brown et al. |
| 5,317,156 A | 5/1994 | Cooper et al. |
| 5,325,704 A | 7/1994 | Mariani et al. |
| 5,351,522 A | 10/1994 | Lura |
| 5,361,771 A | 11/1994 | Craine et al. |

(Continued)

FOREIGN PATENT DOCUMENTS

DE    19607646 A1    9/1997

(Continued)

OTHER PUBLICATIONS

Hong C. et al., "Carbon Nanotube-Enhanced Electrochemical DNA Biosensor for DNA Hybridization Detection" (2003), *Anal. Bioanal. Chem.*, 375:287-293.

(Continued)

*Primary Examiner*—Long V. Le
*Assistant Examiner*—Jacqueline A. DiRamio
(74) *Attorney, Agent, or Firm*—Saliwanchik, Lloyd & Saliwanchik

(57) ABSTRACT

Systems and methods for the ex vivo diagnostic analysis of samples of bodily fluids, including exhaled breath and blood. The present invention uses nanostructure-based assemblies in combination with sensor technology to provide an efficient and accurate means for identifying the presence of a target analyte/biomarker in a sample of bodily fluid. In a preferred embodiment, the nanostructure-based assemblies of the present invention include detecting means such as RNA oligonucleotide chains or "apparatus" and releasable surrogate markers such as DMSO.

11 Claims, No Drawings

U.S. PATENT DOCUMENTS

| | | | |
|---|---|---|---|
| 5,409,839 A | 4/1995 | Balestrieri et al. | |
| 5,425,374 A | 6/1995 | Ueda et al. | |
| 5,447,165 A | 9/1995 | Gustafsson | |
| 5,453,359 A | 9/1995 | Gargan et al. | |
| 5,465,608 A | 11/1995 | Lokshin et al. | |
| 5,466,700 A | 11/1995 | Batenhorst et al. | |
| 5,482,601 A | 1/1996 | Ohshima et al. | |
| 5,495,744 A | 3/1996 | Ueda et al. | |
| 5,501,212 A | 3/1996 | Psaros | |
| 5,528,924 A | 6/1996 | Wajid et al. | |
| 5,547,878 A | 8/1996 | Kell | |
| 5,558,083 A | 9/1996 | Bathe et al. | |
| 5,560,352 A | 10/1996 | Heim et al. | |
| 5,571,401 A * | 11/1996 | Lewis et al. | 205/787 |
| 5,573,005 A | 11/1996 | Ueda et al. | |
| 5,573,955 A | 11/1996 | Khanna et al. | |
| 5,605,612 A | 2/1997 | Park et al. | |
| 5,634,517 A | 6/1997 | Linden et al. | |
| 5,645,072 A | 7/1997 | Thrall et al. | |
| 5,716,852 A | 2/1998 | Yager et al. | |
| 5,756,879 A | 5/1998 | Yamagishi et al. | |
| 5,771,890 A | 6/1998 | Tamada | |
| 5,776,783 A | 7/1998 | Kell | |
| 5,783,154 A | 7/1998 | Althainz et al. | |
| 5,783,449 A | 7/1998 | Kuznetsov | |
| 5,795,787 A | 8/1998 | Silkoff et al. | |
| 5,801,297 A | 9/1998 | Mifsud et al. | |
| 5,826,577 A | 10/1998 | Perroz et al. | |
| 5,830,412 A | 11/1998 | Kimura et al. | |
| 5,861,254 A | 1/1999 | Schneider et al. | |
| 5,866,434 A * | 2/1999 | Massey et al. | 436/526 |
| 5,891,398 A | 4/1999 | Lewis et al. | |
| 5,900,552 A | 5/1999 | Chu et al. | |
| 5,918,257 A | 6/1999 | Mifsud et al. | |
| 5,925,014 A | 7/1999 | Teeple, Jr. | |
| 5,928,167 A | 7/1999 | Wagner et al. | |
| 5,932,877 A | 8/1999 | Braig et al. | |
| 5,945,069 A | 8/1999 | Buehler | |
| 5,950,630 A | 9/1999 | Portwood et al. | |
| 5,954,685 A | 9/1999 | Tierney | |
| 5,958,896 A | 9/1999 | Renshaw et al. | |
| 5,962,335 A | 10/1999 | Katzman | |
| 5,971,937 A | 10/1999 | Ekstrom | |
| 5,996,586 A | 12/1999 | Phillips | |
| 6,007,775 A | 12/1999 | Yager | |
| 6,010,459 A | 1/2000 | Silkoff et al. | |
| 6,025,200 A | 2/2000 | Kaish et al. | |
| 6,057,162 A | 5/2000 | Rounbehler et al. | |
| 6,063,243 A | 5/2000 | Zettl et al. | |
| 6,067,167 A | 5/2000 | Atkinson et al. | |
| 6,074,345 A | 6/2000 | Van Oostrom et al. | |
| 6,085,576 A | 7/2000 | Sunshine et al. | |
| 6,094,681 A | 7/2000 | Shaffer et al. | |
| 6,097,485 A | 8/2000 | Lievan | |
| 6,120,443 A | 9/2000 | Cohen-Laroque | |
| 6,131,571 A | 10/2000 | Lampotang et al. | |
| 6,136,801 A | 10/2000 | Kell | |
| 6,153,147 A | 11/2000 | Craig | |
| 6,180,414 B1 | 1/2001 | Katzman | |
| 6,186,977 B1 | 2/2001 | Andrews et al. | |
| 6,190,858 B1 | 2/2001 | Persaud et al. | |
| 6,203,814 B1 | 3/2001 | Fisher et al. | |
| 6,216,690 B1 | 4/2001 | Keitel et al. | |
| 6,221,026 B1 | 4/2001 | Phillips | |
| 6,234,006 B1 | 5/2001 | Sunshine et al. | |
| 6,237,397 B1 | 5/2001 | Shinar et al. | |
| 6,244,096 B1 | 6/2001 | Lewis et al. | |
| 6,248,078 B1 | 6/2001 | Risby et al. | |
| 6,251,082 B1 | 6/2001 | Rayburn | |
| 6,261,783 B1 | 7/2001 | Jayasena et al. | |
| 6,264,913 B1 | 7/2001 | Wagner | |
| 6,277,081 B1 | 8/2001 | Susi et al. | |
| 6,283,953 B1 | 9/2001 | Ayer et al. | |
| 6,303,316 B1 | 10/2001 | Kiel et al. | |
| 6,305,212 B1 | 10/2001 | Drzewiecki | |
| 6,312,390 B1 | 11/2001 | Phillips | |
| 6,319,724 B1 | 11/2001 | Lewis et al. | |
| 6,328,708 B1 | 12/2001 | Georgieff | |
| 6,341,520 B1 | 1/2002 | Satoh et al. | |
| 6,363,772 B1 | 4/2002 | Berry | |
| 6,387,329 B1 | 5/2002 | Lewis et al. | |
| 6,399,302 B1 | 6/2002 | Lannigan et al. | |
| 6,416,479 B1 | 7/2002 | Seidman | |
| 6,455,319 B1 | 9/2002 | Lewis et al. | |
| 6,467,333 B1 * | 10/2002 | Lewis et al. | 73/31.05 |
| 6,479,019 B1 | 11/2002 | Goldstein et al. | |
| 6,495,824 B1 | 12/2002 | Atkinson | |
| 6,511,453 B1 | 1/2003 | Georgieff | |
| 6,558,626 B1 | 5/2003 | Aker et al. | |
| 6,589,727 B1 | 7/2003 | Klenerman et al. | |
| 6,597,438 B1 | 7/2003 | Cabuz et al. | |
| 6,598,459 B1 * | 7/2003 | Fu | 73/23.34 |
| 6,599,253 B1 | 7/2003 | Baum et al. | |
| 6,599,281 B1 | 7/2003 | Struys et al. | |
| 6,620,800 B1 | 9/2003 | Roberts, II | |
| 6,631,333 B1 | 10/2003 | Lewis et al. | |
| 6,680,377 B1 | 1/2004 | Stanton et al. | |
| 6,727,075 B1 | 4/2004 | Fitzgerald et al. | |
| 6,755,783 B1 | 6/2004 | Cosentino et al. | |
| 2001/0021815 A1 | 9/2001 | Katzman et al. | |
| 2001/0041366 A1 | 11/2001 | Lewis et al. | |
| 2001/0046674 A1 | 11/2001 | Ellington | |
| 2001/0050228 A1 | 12/2001 | Jaeger | |
| 2001/0055544 A1 | 12/2001 | Copp | |
| 2002/0007249 A1 | 1/2002 | Cranley et al. | |
| 2002/0007687 A1 | 1/2002 | Zimmermann et al. | |
| 2002/0014236 A1 | 2/2002 | Dittmann et al. | |
| 2002/0017300 A1 | 2/2002 | Hickle et al. | |
| 2002/0034757 A1 | 3/2002 | Cubicciotti | |
| 2002/0068295 A1 | 6/2002 | Madou et al. | |
| 2002/0173729 A1 | 11/2002 | Viertio-Oja et al. | |
| 2002/0177232 A1 | 11/2002 | Melker et al. | |
| 2003/0004426 A1 | 1/2003 | Melker et al. | |
| 2003/0008407 A1 | 1/2003 | Fu | |
| 2003/0059820 A1 | 3/2003 | Vo-Dinh | |
| 2003/0087239 A1 | 5/2003 | Stanton et al. | |
| 2003/0119065 A1 | 6/2003 | Lin et al. | |
| 2003/0139681 A1 | 7/2003 | Melker et al. | |
| 2003/0216660 A1 | 11/2003 | Ben-Oren et al. | |
| 2004/0027246 A1 | 2/2004 | Aguglia | |
| 2004/0101477 A1 | 5/2004 | Leyland-Jones | |
| 2005/0065446 A1 | 3/2005 | Talton | |

FOREIGN PATENT DOCUMENTS

| | | |
|---|---|---|
| DE | 29902593 | 8/1999 |
| EP | 0 370 151 A1 | 5/1990 |
| EP | 0 979 997 A1 | 2/2000 |
| GB | 829409 A | 3/1960 |
| GB | 2 309 166 A | 7/1997 |
| GB | 2 329 245 A | 3/1999 |
| JP | 08313407 A | 11/1996 |
| JP | 09196915 A | 7/1997 |
| WO | WO 87/02773 A1 | 5/1987 |
| WO | WO 92/10749 A1 | 6/1992 |
| WO | WO 95/08113 A1 | 3/1995 |
| WO | WO 95/31718 A1 | 11/1995 |
| WO | WO 98/57145 | 12/1998 |
| WO | WO 99/12471 A3 | 3/1999 |
| WO | WO 99/66304 A1 | 12/1999 |
| WO | WO 00/25108 A1 | 5/2000 |
| WO | WO 00/67820 A1 | 11/2000 |
| WO | WO 00/79243 A1 | 12/2000 |
| WO | WO 01/34024 A1 | 5/2001 |

| | | |
|---|---|---|
| WO | WO 01/93743 A2 | 12/2001 |
| WO | WO 02/079514 | 10/2002 |
| WO | WO 03/016901 | 2/2003 |
| WO | WO 03/045473 A1 | 6/2003 |
| WO | WO 2004/065404 | 8/2004 |

OTHER PUBLICATIONS

Pantarotto D. et al., "Synthesis, Structural Characterization, and Immunological Properties of Cabon Nanotubes Functionalized with Peptides" (2003), *J. Am. Chem. Soc.*, 125:6160-6164.

Ballantine, DS. et al. "Surface Acoustic Wave Devices for Chemical Analysis," *Anal. Chem.* (1989), vol. 61, No. 11, pp. 704A-712A.

Brody, EN. et al. "Aptamers as Therapeutic and Diagnostic Agents," *Reviews in Molecular Biotechnology* (2000), vol. 74, pp. 5-13.

Brody et al. "The use of Aptamers in Large Arrays for Molecular Diagnostics," *Molecular Diagnosis* (1999), vol. 4, No. 4, pp. 3811-388.

Chandiok, S. et al. "Screening for Bacterial vaginosis: A Novel Application of Artificial Nose Technology," *Journal of Clinical Pathology* (1997), vol. 50, pp. 790-791.

Fang, M. et al. "Detection of Organic Chemicals by SAW Sensor Array," *Sensors and Actuators* (1999), vol. B56, pp. 155-157.

Fischer et al. "A man-portable chemical sniffer utilizing Novel Fluorescent polymers for detection of ultra-trace concentrations of explosives emanating from landmines," *Nomadics Inc.* (2000), pp. 1-10.

Ganga-Zandzou, P.S. et al. "A 13C-urea breath test in children with *Helicobacter pylori* infection: validity of the use of a mask to collect exhaled breath sample," *Acta. Paediatr.* (2001), vol. 90, pp. 232-233.

Grate, JW et al. "Determination of Partition Coefficients from Surface Acoustic Wave Vapor Senor Responses and Correlation with Gas-Liquid Chromatographic Partition Coefficients," *Anal. Chem.* (1998), vol. 60, pp. 869-875.

Groves, W. et al. "Analyzing organic vapors in exhaled breath using a surface acoustic wave sensor array with preconcentration: Selection and characterization of the preconcentrator absorbent," *Analytica Chimica Acta* (1998), vol. 371, pp. 131-143.

Hanson, C.W. et al. "The use of a novel 'Electronic Nose' to diagnose the presence of intrapulmonary infection," *Anesthesiology* (1997), vol. 87, No. 3A, abstract A269.

Liebich et al. "Volatile Substances in Blood Serum: a Profile Analysis and Quantitative Determination," *Journal of Chromatography* (1977), vol. 142, pp. 505-516.

Mueller et al. "Experience in mass spectrometric identification in acute poisoning," *Beitr. Diagn. Ther, Akuter. Intox., Vortr. Symp. 4th* (1982), pp. 126-134, Abstract Only.

Parry, A.D. et al. "Leg Ulcer Odour Detection Identifies β-haemolytic *Streptococcal* Infection," *Journal of Wound Care* (1995). vol 4, No. 9, pp. 404-406.

Paviou and Turner. "Sniffing out the truth: Clinical Diagnosis Using the Electronic Nose," *Clin. Chem. Lab. Med.* (2000), vol. 38, No. 2, pp. 99-112.

Perri, F. "Diagnosis of *Helicobacter pylori* infection: which is best? The urea breath test," *Dig. Liver. Dis.* (2000), vol. 32, Supp. 3, pp. S196-198.

Rogers et al. "Fiber-optic biosensors based on total internal-reflection fluorescence," *American Chemical Society* (1992), Ch. 13, pp. 165-173.

Stojanovic et al. "Aptamer—based Folding Fluorescent Sensor for Cocaine," *J. Am. Chem. Soc.* (2001), vol. 123, pp. 4928-4931.

Tracqui, A. et al. "Systematic Toxicological Analysis Using HPLC/DAD," *Journal of Forensic Sciences* (1995), vol. 40, No. 2, pp. 254-262.

Wohltjen, H. et al. "Vapor Detection with Surface Acoustic Wave Microsensors," *Chemical Sensors and Microinstrumentation* (1989), pp. 157-175.

U.S. Appl. No. 09/708,789, filed Nov. 8, 2000, Lampotang et al.

Dickinson, T. A. et al., "Current Trends in 'Artificial-Nose' Technology," *Tib Tech*, 1998, 16:250-258.

Frauendorf et. al., "Detection of Small Organic Analytes by Fluorescing Molecular Switches," *Bioorganic & Medicinal Chemistry 9*, (2001), pp. 2521-2524.

Fujita et. al., "A Simple Method for Dectecting Plasma Propofol," *Anesth. Analog.*, 2000, 90:1452-1454.

Hammon III, W. S. et al., "Forensic GPR: Finite-Difference Simulations of Responses From Buried Human Remains," *Journal of Applied Geophysics*, (2000), 45:171-186.

Huang et. al., "Depth of Anesthesia Estimating & Propofol Delivery System," Aug. 1, 1996, .rpi.edu/~royr/roy_descpt.html.

Jayasena, "Aptamers: An Emerging Class of Molecules That Rival Antibodies in Diagnositcs," *Clinical Chemistry*, 1999, 45(9):1628-1650.

Kenny, "Target-Controlled Infusions—Pharmacokinetic and Pharmacodynamic Variations," .anaesthesiologie.med.uni-erlangen.de/esctaic97/a_kenny.htm.

Kuipers et al., "First-pass Lung Uptake and Pulmonary Clearance of Propofol," *Anesthesiology*, (1999), 91:1780-1787.

Miller III, E. R. et al., "Association Between Cigarette Smoking and Lipid Peroxidation in a Controlled Feeding Study," *Circulation*, (1997), 96(4):1097-1101.

Phillips, M., "Breath Tests in Medicine," *Scientific American*, 1992, pp. 52-57.

Pilar Kraman, "Prescription Drug Diversion," *Trends Alert* provided by the Council of State Government at csg.org (Apr. 2004).

Stuart, B. H. et al., "Studies of Adipocere Using Diffuse Reflectance Infrared Spectroscopy," *Vibrational Spectroscopy*, 24:233-242, (2000).

Stubbs, D. D. et al., "Investigation of Cocaine Plumes Using Surface Acoustic Wave Immunoassay Sensors," *Annal. Chem.*, 75:6231-6235, (2003).

U.S. Food and Drug Administration, "FDA White Paper, Protecting the Public Health: FDA Pursues and Aggressive Enforcement Strategy," fda.gov/oc/whitepapers/enforce.html (Jun. 30, 2003).

U.S. Food and Drug Administration, "New FDA Initiative to Combat Counterfeit Drugs," fda.gov/oc/initiatives/counterfeit/backgrounder.html (Jul. 2, 2004).

United States Department of Justice, "Review of the Drug Enforcement Administration's (DEA) Control of the Diversion of Controlled Pharmaceuticals," Report No. I-2002-010 www.usdoj.gov/oig/inspection/DEA/0210/background.htm (Sep. 2002).

Vass, A., "Beyond the Grave—Understanding Human Decomposition," *Microbiology Today*, Nov. 2001, 28:190-192.

Vass, A. et al., "Decomposition Chemistry of Human Remains: A New Methodology for Determining the Postmortem Interval," *J. Forensic Sci.*, (2002), 47(3):542-553.

Vass, A. et al., "Detection of Buried Human Remains Using Bioreporter Fluorescence," U.S. Dept. of Energy Report, Y/NSP-726 (2001).

\* cited by examiner

APPLICATION OF NANOTECHNOLOGY AND SENSOR TECHNOLOGIES FOR EX-VIVO DIAGNOSTICS

CROSS-REFERENCE TO RELATED APPLICATION

This application is a continuation-in-part of co-pending U.S. application Ser. No. 10/154,201, filed May 22, 2002; which claims the benefit of U.S. application Ser. No. 60/292,962, filed May 23, 2001. This application is also a continuation-in-part of co-pending U.S. application Ser. No. 10/274,829, filed Oct. 21, 2002; and a continuation-in-part of co-pending U.S. application Ser. No. 10/345,532, filed Jan. 16, 2003, all of which are hereby incorporated by reference herein in their entirety, including any figures, tables, or drawings.

GOVERNMENT SUPPORT

The subject matter of this application has been supported in part by a research grant from the National Science Foundation (Grant Number NSF: EEC 02-10580). Accordingly, the government may have certain rights in this invention.

BACKGROUND OF THE INVENTION

There is a great need for the development of efficient and accurate systems for the diagnosis of a variety of medical conditions, disorders, and diseases. A means for rapid and accurate analysis and diagnosis of ex vivo bodily fluid samples at the point of care is particularly desirable. This requires an effective means for identifying in a patient the presence of specific chemical and/or biological agents including, but not limited to, nucleic acids, proteins, illicit drugs, toxins, pharmaceuticals, carcinogens, poisons, allergens, and infectious agents.

Current methods of detecting such chemical or biological agents entail extraction of a sample into organic solvents, followed by analysis using stand-alone analytical systems such as gas-liquid chromatography and/or mass spectroscopy. These methods are time-consuming and often expensive. Moreover, certain analytes/biomarkers of interest (i.e., nucleic acids, carcinogens, or toxins) are not readily detected by standard chemical tests utilized in a typical clinical physician's office or even in hospital departments. Further, on-site test devices for accurate analyte/biomarker detection are not presently available. The development of a biosensor device that could accurately and efficiently detect/screen for chemical and biological agents in bodily fluid samples would therefore provide a significant cost and time benefit.

Three recent advancements in medicine are particularly germane to expanding the potential of detecting chemical and/or biological agents, especially with regard to the diagnosis of disease: nanotechnology, biodetectors (biosensors), and the identification of biomarkers for specific diseases and/or conditions. Nanotechnology, such as nanoparticles, offers many advantages when used for applications such as sensor technology for detecting chemical agents. For example, nanoparticle-bound surfaces can form a sensor effective in detecting a target chemical agent.

The term "biodetectors" or "biosensors" relates to the use of naturally occurring and/or synthetic compounds as highly specific and extraordinarily sensitive detectors of various types of molecules and markers of disease. Naturally-occurring compounds such as antibodies have been used to provide molecular recognition for a wide variety of target molecules in diagnostic assays. Alternatively, synthetic compounds have been manufactured that mimic naturally-occurring mechanisms of DNA, RNA, and protein synthesis in cells to facilitate the detection of target chemical or biological agents.

Aptamers have recently been identified as potentially effective biosensors for molecules and compounds of scientific and commercial interest (see Brody, E. N. and L. Gold, "Aptamers as therapeutic and diagnostic agents," *J. Biotechnol.*, 74(1):5–13 (2000) and Brody et al., "The use of aptamers in large arrays for molecular diagnostics," *Mol. Diagn.*, 4(4):381–8 (1999)). For example, aptamers have demonstrated greater specificity and robustness than antibody-based diagnostic technologies. In contrast to antibodies, whose identification and production completely rest on animals and/or cultured cells, both the identification and production of aptamers takes place in vitro without any requirement for animals or cells.

Aptamer synthesis is potentially far cheaper and reproducible than antibody-based diagnostic tests. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than those antibody-based diagnostic tests. These inherent characteristics of aptamers make them attractive for diagnostic applications.

A number of "molecular beacons" (often fluorescence compounds) can be attached to aptamers to provide a means for signaling the presence of and quantifying a target chemical or biological agent. For instance, an aptamer specific for cocaine has recently been synthesized (Stojanovic; M. N. et al., "Aptamer-based folding fluorescent sensor for cocaine," *J. Am. Chem. Soc.*, 123(21):4928:31 (2001)). A fluorescence beacon, which quenches when cocaine is reversibly bound to the aptamer is used with a photodetector to quantify the concentration of cocaine present. Aptamer-based biosensors can be used repeatedly, in contrast to antibody-based tests that can be used only once.

Of particular interest as a beacon are amplifying fluorescent polymers (AFP). AFPs with a high specificity to TNT and DNT have been developed. It has been noted that a detector based on AFP technology, with high specificity to TNT and DNT, can also detect propofol, an intravenous anesthetic agent, in extremely low concentrations. The combination of AFP and aptamer technologies holds the promise of robust, reusable biosensors that can detect compounds in minute concentrations with high specificity.

The term "biomarker" refers to a biochemical in the body that has a particular molecular trait to make it useful for diagnosing a condition, disorder, or disease and for measuring or indicating the effects or progress of a condition, disorder, or disease. For example, common biomarkers found in a person's bodily fluids (i.e., breath or blood), and the respective diagnostic conditions of the person providing such biomarkers include, but are not limited to, acetaldehyde (source: ethanol; diagnosis: intoxication), acetone (source: acetoacetate; diagnosis: diet; ketogenic/diabetes), ammonia (source: deamination of amino acids; diagnosis: uremia and liver disease), CO (carbon monoxide) (source: $CH_2Cl_2$, elevated % COH; diagnosis: indoor air pollution), chloroform (source: halogenated compound), dichlorobenzene (source: halogenated compounds), diethylamine (source: choline; diagnosis: intestinal bacterial overgrowth), H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma, metabolite; diagnosis: bronchogenic carcinoma), pentane sulfides and sulfides (source: lipid peroxidation; diagnosis: myocardial infarction), $H_2S$ (source: metabolism; diagnosis: periodontal disease/ovulation), MeS (sucrose: metabolism; diagnosis: cirrhosis), and $Me_2S$ (source: infection; diagnosis: trench mouth).

Mechanisms of drug metabolism are extremely complex and are influenced by a number of factors including competitive binding on protein and red blood cells with other molecules, enzymatic activity, particularly in the liver, protein, and red blood cell concentration and a myriad of other factors. Currently, very little technology is available that can measure drug concentration in a patient in real-time, especially at the point of care, and thereby allow convenient determination of pharmacokinetics and pharmacodynamics of multiple compounds in real-time.

Accordingly, there are a number of medical conditions that can be monitored by detecting and/or measuring biomarkers present in a person's breath (including breath condensates or aerosolized particles) or other bodily fluids. While there has been technology generated towards the synthesis and use of aptamers and other multimolecular devices such as biosensors, very little technology exists to address the use of aptamers, or other biodetectors, in combination with nanoparticles to form sensors for the ex vivo diagnosis of disease and/or detection of a naturally occurring or synthetic compounds. It is therefore desirable to provide a low-cost means for accurately and timely detecting and/or measuring the presence of metabolites in a person's bodily fluids in low concentrations.

BRIEF SUMMARY

The present invention provides unique systems and methods for the ex vivo detection of analytes/biomarkers of interest in samples of bodily fluids. The invention comprises a nanostructure-based assembly that is applied to bodily fluid samples collected from a patient. In accordance with the present invention, a nanostructure-based assembly contains (a) a nanoparticle, which includes (b) a means for detecting a target analyte/biomarker (i.e., aptamers, antibodies); and (c) at least one surrogate marker. These components can be attached to any surface of the nanoparticle.

In operation, a sample of bodily fluid is collected from a patient and the nanostructure-based assembly of the invention is applied to the sample. When the detecting means detects a target analyte/biomarker, the surrogate marker is released from the nanoparticle. Because surrogate markers are released from nanoparticles only in the presence of a target analyte/biomarker, detection of surrogate markers provides notice of the presence of the target analyte/biomarker in the patient and consequently, allows diagnosis of the specific condition, disorder, or disease associated with the target analyte/biomarker. Not only do surrogate markers signal the presence of the target analyte/biomarker, but they also provide a means for quantifying the concentration of the analyte/biomarker of interest present in the sample of bodily fluid.

In accordance with the present invention, the detecting means includes well-known biodetectors or biosensors. Such biodetectors to biosensors include naturally occurring and/or synthetic compounds having high specificity and sensitivity to chemical and/or biological compounds of interest. Suitable biodetectors or biosensors of the invention include, but are not limited to, antibodies, proteins, and aptamers.

The surrogate marker of the invention is a compound that is readily detectable in bodily fluid samples. In preferred embodiments, the surrogate marker is a volatile compound (i.e., dimethyl sulfoxide—DMSO).

According to the invention, a sample of bodily fluid includes, but is not limited to, exhaled breath (including cough, sneeze), blood, urine, sweat, mucous, semen, bile, feces, saliva, lymph fluid, blood plasma, amniotic fluid, glandular fluid, sputum, and cerebral spinal fluid. The bodily fluid sample is analyzed for the presence of the surrogate marker, which indicates the presence of the target analyte/biomarker in the patient and consequently, allows for the diagnosis of the condition, disease, or disorder associated with the target analyte/biomarker.

For analysis of bodily fluid samples to detect the presence of the surrogate marker, sensor technology is applied in accordance with the present invention. Contemplated sensor technology includes, but is not limited to, previously disclosed sensor technology such as semiconductor gas sensor technology, conductive polymer gas sensor technology, surface acoustic wave gas sensor technology, and immunoassays.

The results from the sensor technology analysis of the bodily fluid samples are optionally provided to the user (or patient) via a reporting means. In one embodiment, the sensor technology includes the reporting means. Contemplated reporting means include a computer processor linked to the sensor technology in which electronic or printed results are provided. Alternatively, the reporting means can include a digital display panel, transportable read/write magnetic media such as computer disks and tapes which can be transported to and read on another machine, and printers such as thermal, laser or ink-jet printers for the production of a printed report. The reporting means can provide the results to the user (or patient) via facsimile, electronic mail, mail or courier service, or any other means of safely and securely sending the report to the patient. Interactive reporting means are also contemplated by the present invention, such as an interactive voice response system, interactive computer-based reporting system, interactive telephone touch-tone system, or other similar system. The report provided to the user (or patient) may take many forms, including a summary of analyses performed over a particular period of time or detailed information regarding a particular bodily fluid sample analysis. Results may also be used to populate a financial database for billing the patient, or for populating a laboratory database or a statistical database.

In one embodiment, the nanoparticle of the nanostructure-based assembly has a hollow body defining an inner void, which contains the surrogate marker. Release of the surrogate marker is controlled by the means for detecting the target analyte/biomarker. In certain embodiments, the detecting means is attached to an end-cap, which covers an opening to the inner void. In other embodiments, the detecting means is attached to the surface of the nanoparticle. The detecting means is designed to undergo a conformational change upon detecting the target analyte/biomarker to affect the release of the surrogate marker from the nanoparticle. With reference to those embodiments in which the detecting means is attached to an end-cap, the conformational change of the detecting means in the presence of a target analyte/biomarker causes the end-cap to detach from the nanoparticle and release the surrogate marker.

In a related embodiment, the detecting means is attached to a surface of the nanoparticle. The detecting means can localize the nanostructure-based assembly to the target analyte/biomarker. When in the presence of the target analyte/biomarker, the controlled release of the surrogate marker is accomplished by the release of an end-cap, which is attached to the nanoparticle via chemically labile bonds. Preferably, the bonds attaching the end-cap to the nanoparticle are sensitive to the target analyte/biomarker.

Alternatively, the surrogate markers may be directly attached to a surface of the nanoparticle via chemically labile bonds that are sensitive to the target analyte/biomarker. Thus, when the nanostructure-based assembly is localized to the target analyte/biomarker by the detecting means, the surrogate markers are released without the need for an end-cap.

Yet another embodiment provides a solid nanoparticle that has the detecting means is attached to the outside surface of the nanoparticle and the surrogate marker is attached to the detecting means. In the presence of a target analyte/biomarker, the detecting means undergoes a conformational change to cause the surrogate marker to be detectable to the user. For example, the detecting means/surrogate marker of the invention can include aptamer-based molecules beacons.

In a preferred embodiment, nanoparticles are in the form of nanotubes, which are defined by a hollow tubular body with an inner void, which contains a surrogate marker. The hollow tubular body has a first end and a second end. The first end of the tubular body is open and a first end-cap bound to a detecting means is positioned over the first open end to close the first end. The second end of the tube is closed or similarly capped as the first end. Preferably, the detecting means is an aptamer.

The advantages of the invention are numerous. First and foremost, for healthcare personnel, the invention provides a method that can readily diagnose a patient's condition (or disorder/disease) based on a small sample of the patient's bodily fluid. Second, the invention is inexpensive and has broad medical applications for detecting a wide range of compounds (including licit and illicit drugs) in samples of bodily fluids.

For example, using the systems and methods of the present invention, emergency room personnel can quickly and effectively determine if someone is suffering from traumatic brain injury (TBI). By mixing nanostructure-based assemblies of the present invention to an ex vivo sample of the injured patient's blood or cerebral spinal fluid and applying sensor technology to the mixture, the present invention can accurately assess the presence and concentration of αII-spectrin breakdown products (biomarkers of TBI) for which the nanostructure-based assemblies are programmed to detect. A resulting advantage of the ability to rapidly detect TBI through a simple and efficient system is the ability to timely treat TBI.

In another embodiment, the nanostructure-based assemblies are designed to detect a protein, prostate specific antigen (PSA), which is produced by prostate cancers. In accordance with the present invention, a detecting means is designed that is specific for PSA (i.e., PSA-aptamer). The detecting means is attached to a surface of the nanoparticle. Also included on or within the nanoparticle is at least one surrogate marker (i.e., DMSO).

To test for the presence of prostate cancer, or a recurrence of prostate cancer, a nanostructure-based assembly designed to detect PSA is mixed with an ex-vivo sample of a patient's bodily fluid (i.e., blood). Where PSA is present in the bodily fluid sample, the PSA interacts with the detecting means, which affects the release of the surrogate marker for detection. Any one of a number of previously disclosed sensor technologies is then used to detect the surrogate marker, which indicates the presence and concentration of PSA in the bodily fluid sample.

Ex vivo analysis of bodily fluids utilizing methods disclosed herein can be applied to a wide range of point of care (POC) diagnostic tests. For example, potential applications include detection of licit and illicit drugs, detection of a wide range of biomarkers related to specific diseases, and detection of any other compounds that appear in bodily fluids. These tests can be highly quantitative because the quantity of surrogate markers released/detectable is proportional to the quantity of a target analyte/biomarker present in a sample of bodily fluid.

Moreover, analysis of bodily fluid samples using the method of the present invention can enable timely interventions for time-sensitive conditions or diseases. For example, it is known that isoprostane levels increase in cerebral spinal fluid and blood after TBI. If isoprostane is readily detectable in bodily fluids (i.e., blood, cerebral spinal fluid) using an isoprostane specific nanostructure-based assembly of the present invention, it can be possible to not only diagnose TBI in a patient but also to evaluate the efficacy of interventions in real-time for TBI. In addition, the method of the present invention can also evaluate pharmacodynamics and pharmacokinetics for drug interventions in individuals.

DETAILED DISCLOSURE

The present invention is directed to the efficient, timely, and accurate analysis of a sample of a patient's bodily fluids to detect and/or quantify analytes/biomarkers indicative of conditions, disorders, or diseases such as intoxication, cancer, cardiac disease, drug abuse, renal failure, liver disease, or diabetes. The systems and methods of the invention use nanostructure-based assemblies that contain a nanoparticle, a means for detecting a target analyte/biomarker, and a surrogate marker. Commonly available sensor technology is used by the present invention to detect the presence of a surrogate marker released from a nanostructure-based assembly in a sample of bodily fluid.

In operation, nanostructure-based assemblies of the invention are mixed with an ex vivo bodily fluid sample collected from a patient. Surrogate markers are generally released into the patient when nanostructure-based assemblies are in the presence of target analytes/biomarkers. Specifically, bioactive interaction between the biodetector/biosensor and the target analyte/biomarker affect the release of the surrogate marker from the nanoparticle. Advantageously, the concentration of the released surrogate marker is proportional to the amount of analyte/biomarker present in the bodily fluid sample, which can be measured using quantitative sensor technology known in the art.

Definition

Unless otherwise stated, the following terms used in the specification and claims have the meanings given below:

The term "aptamer," as used herein, refers to a non-naturally occurring oligonucleotide chain that has a specific action on a target analyte/biomarker of interest. A specific action includes, but is not limited to, binding the target analyte/biomarker, catalytically changing the target analyte/biomarker, and reacting with the target analyte/biomarker in a way which modifies/alters the analyte/biomarker or the functional activity of the analyte/biomarker. The aptamers of the invention preferably specifically bind to a target analyte/biomarker and/or react with the target analyte/biomarker in a way which modifies/alters the analyte/biomarker or the functional activity of the analyte/biomarker.

Aptamers include nucleic acids that are identified from a candidate mixture of nucleic acids. In a preferred embodiment, aptamers include nucleic acid sequences that are substantially homologous to the nucleic acid ligands isolated by the SELEX method. Substantially homologous is meant a degree of primary sequence homology in excess of 70%, most preferably in excess of 80%.

The "SELEX" methodology, as used herein, involves the combination of selected nucleic acid ligands, which interact with a target analyte/biomarker in a desired action, for example binding to a protein, with amplification of those selected nucleic acids. Optional iterative cycling of the selection/amplification steps allows selection of one or a small number of nucleic acids, which interact most strongly with the target analyte/biomarker from a pool, which contains a very large number of nucleic acids. Cycling of the selection/amplification procedure is continued until a selected goal is achieved. The SELEX methodology is described in the following U.S. patents and patent applications: U.S. patent application Ser. No. 07/536,428 and U.S. Pat Nos. 5,475,096 and 5,270,163.

The term "indicator aptamers," as used herein, refers to aptamers to which molecular beacons are attached, such as those described in U.S. Pat. Nos. 6,399,302 and 5,989,823.

The term "molecular beacons," as used herein, refers to a molecule or group of molecules (i.e., a nucleic acid molecule hybridized to an energy transfer complex or chromophore(s)) that can become detectable and can be attached to a biodetector/biosensor under preselected conditions. For example, an embodiment of the present invention includes an aptamer-bound fluorescence beacon that (a) quenches when a target analyte/biomarker is reversibly bound to the aptamer and (b) is detectable with a photodetector to quantify the concentration of target analyte/biomarker present.

As used herein, "analytes" and "biomarkers" are used interchangeably (i.e., "analyte/biomarker") to refer to naturally occurring and/or synthetic compounds, which are a marker of a condition (i.e., drug abuse), disease state (i.e., infectious diseases), disorder (i.e., neurological disorders), or a normal or pathologic process that occurs in a patient (i.e., drug metabolism). The term "analyte" or "biomarker," as used herein, can refer to any substance, including chemical and/or biological agents that can be measured in an analytical procedure.

Analytes/biomarkers that can be detected using the present invention include, but are not limited to, the following metabolites or compounds commonly found in bodily fluids: acetaldehyde (source: ethanol; diagnosis: intoxication), acetone (source: acetoacetate; diagnosis: diet or ketogenic/diabetes), ammonia (source: deamination of amino acids; diagnosis: uremia and liver disease), CO (carbon monoxide) (source: $CH_2Cl_2$, elevated % COHb; diagnosis: indoor air pollution); chloroform (source: halogenated compounds), dichlorobenzene (source: halogenated compounds), diethylamine (source: choline; diagnosis: intestinal bacterial overgrowth); H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), $H_2S$ (source: metabolism; diagnosis: periodontal disease/ovulation), MeS (source: metabolism; diagnosis: cirrhosis), $Me_2S$ (source: infection; diagnosis trench mouth), αII-spectrin breakdown products and/or isoprostanes (source: cerebral spinal fluid, blood; diagnosis: traumatic or other brain injuries); prostate specific antigen (source: prostate cells; diagnosis: prostate cancer); and GLXA (source: glycolipid in Chlamydia; diagnosis: Chlamydia).

Additional analytes/biomarkers that can be detected using the present invention include, but are not limited to, illicit, illegal, and/or controlled substances including drugs of abuse (i.e., amphetamines, analgesics, barbiturates, club drugs, cocaine, crack cocaine, depressants, designer drugs, ecstasy, Gamma Hydroxy Butyrate—GHB, hallucinogens, heroin/morphine, inhalants, ketamine, lysergic acid diethylamide—LSD, marijuana, methamphetamines, opiates/narcotics, phencyclidine—PCP, prescription drugs, psychedelics, Rohypnol, steroids, and stimulants); allergens (i.e., pollen, spores, dander, peanuts, eggs, and shellfish); toxins (i.e., mercury, lead, other heavy metals, and *Clostridium Difficile* toxin); carcinogens (i.e., acetaldehyde, beryllium compounds, chromium, dichlroodiphenyltrichloroethane (DDT), estrogens, N-methyl-N'-nitro-N-nitrosoguanidine (MNNG), and radon); and infectious agents (i.e., *Bordettella bronchiseptica*, citrobacter, *Escherichi coli*, hepatits viruses, herpes, immunodeficiency viruses, influenza virus, *listeria*, micrococcus, mycobacterium, rabies virus, rhinovirus, rubella virus, *Salmonella*, and yellow fever virus).

The term "bodily fluid," as used herein, refers to a mixture of molecules obtained from a patient. Bodily fluids include, but are not limited to, exhaled breath, whole blood, blood plasma, urine, semen, saliva, lymph fluid, meningal fluid, amniotic fluid, glandular fluid, sputum, feces, sweat, mucous, and cerebrospinal fluid. Bodily fluid also includes experimentally separated fractions of all of the preceding solutions or mixtures containing homogenized solid material, such as feces, tissues, and biopsy samples.

The term "biodetector/biosensor," as used herein, refers to the use of naturally-occurring and/or synthetic compounds as highly specific and sensitive detectors of various types of analytes/biomarkers. Naturally-occurring compounds such as antibodies, proteins, receptor ligands, and receptor proteins have been used to provide molecular recognition for a wide variety of target molecules in diagnostic assays. Alternatively, synthetic compounds such as aptamers have been manufactured that mimic naturally occurring mechanisms of DNA, RNA, and protein synthesis in cells to facilitate detection of target analytes/biomarkers.

The term "ex vivo," as used herein, refers to an environment outside of a patient. Accordingly, a sample of exhaled breadth collected from a patient is an ex vivo sample of bodily fluid as contemplated by the subject invention.

The term "surrogate marker," as used herein, refers to a molecule or compound that is detectable by means of its physical or chemical properties. As such, surrogate markers are detectable by a number of sensor technologies known in the art including, but not limited to, flow cytometers, semiconductive gas sensors; mass spectrometers; infrared (IR), ultraviolet (UV), visible, or fluorescence spectrophotometers; gas chromatography, conductive polymer gas sensor technology; surface acoustic wave gas sensor technology; immunoassay technology, and amplifying fluorescent polymer (AFP) sensor technology.

A "patient," as used herein, describes an organism, including mammals, from which bodily fluid samples are collected in accordance with the present invention. Mammalian species that benefit from the disclosed systems and methods of diagnosis include, and are not limited to, apes, chimpanzees, orangutans, humans, monkeys; and domesticated animals (e.g., pets) such as dogs, cats, mice, rats, guinea pigs, and hamsters.

Nanoparticles

Nanostructure-based assemblies offer timely, and effective detection and notification of a condition, disorder, or disease in a patient via ex vivo analysis. Such assemblies are based on nanoparticles, which provide a mechanism for the detection of a target analyte/biomarker in a bodily fluid sample as well as a mechanism for the release of detectable surrogate markers to signal the presence of a target analyte/biomarker.

According to the present invention, nanoparticles can be produced in a wide range of sizes and shapes, and composed of a wide range of materials, or combination of materials, optimized for ex-vivo analysis. Contemplated shapes include, but are not limited to, spherical, elliptical, cubic, cylindrical, tetrahedron, polyhedral, irregular-prismatic icosahedral, and cubo-octahedral forms. Nanoparticles intended for ex-vivo use are of any dimension, preferably with a maximum dimension less than 500 nm, so as to ensure proper distribution at the cellular level. The "maximum dimension" of a nanoparticle is the maximum distance between any two points in the nanoparticle. In a preferred embodiment, the nanoparticles are in the form of tubular bodies (also known as "nanotubes"), which are either hollow or solid and include either open ends or one or both closed ends.

Methods of preparation of nanoparticles are well known in the art. For example, the preparation of monodisperse sol-gel silica nanospheres using the well-known Stober process is described in Vacassy, R. et al., "Synthesis of Microporous Silica Spheres," *J. Colloids and Interface Science,* 227, 302 (2000).

Nanoparticles, in accordance with the present invention, can be prepared from a single material or a combination of materials. For example, nanotubes can be prepared from either one or a combination of materials including, but not limited to, polymers, semiconductors, carbons, or $Li^+$ intercalation materials. Metal nanoparticles include those made from gold or silver. Semi-conductor nanoparticles include those made from silicon or germanium. Polymer nanoparticles include those made from biocompatible or biodegradable polymers. The ability to make nanoparticles from a wide variety of materials or combination of materials allows the creation of nanoparticles with desired biochemical properties such as biocompatibility, including immunogenic compatibility, and/or, biodegradability.

Nanoparticles of the present invention can be synthesized using a template synthesis method. For example, nanoparticles can be synthesized using templates prepared from glass (Tonucci, R. J. et al., *Science* 258, 783 (1992)), xeolite (Beck, J. S. et al., *J. Am. Chem. Soc.,* 114, 10834 (1992)), and a variety of other materials (Ozin, G. A., *Adv. Mater.,* 4, 612 1992)). Alternatively, nanoparticles can be prepared using a self-assembly process, as described in Wang, Z. L., "Structural Analysis of Self-Assembling Nanocrystal Superlattices," *Adv. Mater.,* 10(1):13–30 (1998).

In one embodiment, a nanostructure-based assembly of the invention contains a nanoparticle, which has one or more surfaces functionalized to allow attachment of biodetectors/biosensors to the surface. Such "functionalized" nanoparticles have at least one surface modified to allow for the directional delivery and/or controlled release of the payload and surrogate marker. In certain embodiments, the nanoparticle is formed with an interior void. Thus, different chemical and/or biochemical functional groups can be applied to the inside and/or outside surfaces of the nanoparticle. Alternatively, one chemical/biochemical species can be applied to the inside surface of the nanoparticle and a second species to the outside surface.

In another embodiment, the nanostructure-based assembly contains a nanoparticle formed with an interior void to contain a surrogate marker and a detechable end-cap with a detecting means attached thereto. In the presence of a target analyte/biomarker, the detecting means mechanically detaches the end-cap from the nanoparticle to release the surrogate marker for analysis by sensor technology.

In a preferred embodiment, the nanoparticle is in the form of a nanotube that is hollow and has a first open end and a second closed end. A surrogate marker is enclosed within the hollow interior of the nanotube. The first open end is blocked with an aptamer-end-cap that prevents the release of the surrogate marker located within the hollow interior of the nanotube.

Upon detecting a target analyte/biomarker by the aptamer attached to an end-cap, the surrogate marker is released with the uncapping of the nanoparticle. The uncapping mechanism may require the use of energy-bearing biomolecular motors such as, but not limited to, the actin-based system (Dickinson, R. B. and D. L. Purich, "Clamped filament elongation model for actin-based motors," *Biophys. J.,* 82:605–617 (2002)). Once the nanoparticle is uncapped, the released surrogate marker can then be detected using sensor technology known in the art including, but not limited to, gas chromatography, electronic noses, spectrophotometers to detect the surrogate marker's infrared (IF), ultraviolet (UV), or visible absorbance or fluorescence, or mass spectrometers.

Nanotubes

Depending upon the application, various types of sensors, for example, aptamers, antibodies/proteins, peptides, or high affinity ligands, can be linked to the uncapping/discharge mechanism of the nanocap-nanostructure-based assemblies of the invention. Thus, the uncapping mechanism can be linked to detection by the sensors on the nanocap-nanotube structure of surface markers on cells types (e.g., cancer cells), proteins in the blood (e.g., PSA for prostate cancer) or drugs in the body (e.g., illicit drugs or therapeutic drugs). These may or may not require the use of energy-bearing biomolecular motors such as, but not limited to, the actin-based system (Dickinson R. B. and Purich D. L., Biophys. . 2002 82:605–617).

In another embodiment, the nanocap (or "end-cap") is attached by electrostatic attraction between the nanocap and the nanotube. The cap is released in response to a change in the ionic strength of the medium according the nanotube. Alternatively, the cap can be held on by hydrogen bonding or by acid and/or basic sites on the nanocap/nanotube. The cap is released by a change in the pH or the surrounding medium. The cap may also be held on by covalent bonds that can be cleaved by a specific enzyme, for example, a hydrolase enzyme.

The sensors can be designed to initiate release of payload contents (such as a surrogate marker) upon detecting stimuli. Such stimuli can include physical stimuli, for example, the temperature, pressure, velocity or acceleration of the nanoparticle; biological stimuli, for example, the presence of normal or abnormal cell types, cellular surface antigens, proteins, oligonucleotides, or toxins; or chemical stimuli, for example, pH, ionic strength, hydration state, redox state, or the presence of therapeutic agents, or toxic drugs such as nerve agents.

For example, one can achieve safe and effective intracellular surrogate marker release by attaching the nanocap to the nanotube with covalent bonds (e.g., S—H bonds) that are broken when a specific chemical signal (e.g., high reducing atmosphere of the cytoplasmic environment of the interior of a mammalian cell) is encountered. The ability to incorporate different types of sensor mechanisms for removal of the cap is an extremely powerful approach to the delivery and release (or uptake) of payload contents in an event- and site-specific manner. Specifically, by linking the uncapping mechanism to various sensing modes, the nanotubes based surrogate marker transport systems can be used to diagnose, treat, and monitor health status. For example, smart nanotubes can detect the appearance of cancer antigens on the walls of cancer cells, cause uncapping which in turn releases an indicator, which in turn makes the urine a distinct color or releases a nontoxic marker which can be readily detected in the breath, and thereby notifies the patient or his/her physician that a cancer cell(s) was encountered in his/her body.

Nanotube technology provides a method for delivering surrogate markers. In one embodiment, this is achieved using nanocaps that are firmly bound to the nanotube when the assembly is outside of the cell but are released, thus opening the nanotube and making the surrogate marker available, when the assembly is partitioned into the cell. For example, this can be accomplished using disulfide chemistry to couple the nanoparticle cap to the nanotube. The disulfide link between the nanotube and its nanocap is ideal because all living cells maintain a reducing environment within their cytoplasm. This contrasts with the oxidizing environment found outside the cell. The tripeptide glutathione (-gluatamyl-cysteinyl-glycine) plays a key role in this process. In its reduced form, glutathione possesses a free sulfhydryl capable of reducing disulfide bonds, forming a disulfide-linked glutathione dimer in the process. This species, in turn, is reduced by nicotinamide-dependent enzymes.

A number of patents and publications describe nanotube technology. For example, U.S. Pat. No. 5,482,601 to Ohshima et al. describes a method for producing carbon nanotubes. Other methods for making and using nanotubes include the non-carbon nanotubes of Zettl et al., U.S. Pat. No. 6,063,243, and the functionalized nanotubes of Fisher et al., U.S. Pat. No. 6,203,814.

For nanotubes, synthesis occurs within the membrane pores of a microporous membrane or other solid, as described in Charles R. Martin, "Nanomaterials: A Membrane-Based Synthetic Approach," *Science*, 266:1961–1966 (1994), using electrochemical or chemical methods. Depending on the membrane and synthetic method used, the nanotubes may be solid or hollow. Template membrane pore diameters can be varied to produce nanotubes having diameters as small as 5 nm to as large as 100 µm. Likewise, the template membrane thickness can be varied to given nanotubes having a length from as small as 5 nm to as large as 100 µm. Preferably, when the nanotube is intended for in vivo use, the nanotube is of length less than 500 µm and diameter less than 200 nm. Especially preferred nanotubes for ex vivo use have a maximum dimension less than 100 nm.

"Track-etch" polymeric or porous alumina membranes can be used in the preparation of nanotubes. Track-etch membranes prepared from polycarbonate and polyester are available from suppliers such as Osmonics (Minnetonka, Minn.) and Whatman (Maidstone, Kent UK). Tracl-etch membranes contain randomly distributed cylindrical pores of uniform diameter than run through the entire thickness of the membrane. Pore diameters as small as 10 nm are commercially available at pore densities of up to $10^9$ pores per square centimeter.

Porous alumina membranes, which are commercially available from Whatman (Maidstone, Kent UK), are prepared electronically from aluminum metal. Pore diameters as small as 5 nm can be achieved at pore densities as high as $10^{11}$ pores per square centimeter. Membranes can be prepared having the membrane thickness from as small as 100 nm to as large as 100 µm.

Nanotubes can be synthesized such that both ends of the nanotube are open. Alternatively, nanotubes having one open end can be synthesized. Solid nanotubes can also be synthesized. Nanotubes with one closed end can be produced by template synthesis. Before the alumina template membrane is removed from the substrate aluminum surface, the pores in the alumina terminate into a non-porous alumina barrier layer (Hornyak, G. L., et al., "Fabrication, Characterization and Optical Properties of Gold-Nanoparticle/Porous-Alumina Composites: The Non-Scattering Maxwell-Garnett Limit," *J. Phys. Chem. B.*, 101:1548–1555 (1997)). This non-porous barrier layer is removed when the alumina membrane is stripped off the aluminum surface. However, if the template synthesis is completed before removal of the alumina from the aluminum, the bottoms of the nanotubes are closed. Dissolution of the alumina then liberates the nanotubes that are closed at one end and open at the other end.

Suitable end-caps used to block a nanotube opening include, for example, nanoparticles having a diameter slightly larger than the inside diameter of the nanotubes so as to occlude the open end of the nanotube. End-caps are any piece of matter and can be composed of materials that are chemically or physically similar (or dissimilar) to the nanotube. The end-cap can be a particle that has a maximum dimension of less than 100 µm. In a preferred embodiment, the end-cap is of a spherical or spheroidal form. However, end-caps of other shapes, including ellipsoidal, cylindrical, and irregular, can also be used.

A suitable end-cap can be attached to a nanotube by covalent bonds. For example, silica nanotubes and particles can be linked by disulphide bonds. Initially, the surface at the ends of silica nanotubes is functionalized with a —SH linker. This can be performed while the nanotubes are still embedded in the pores of the template membrane. This allows activation of the end surface without changing the chemical properties of the outer surface of the nanotubes.

If necessary, the inner surfaces of the nanotubes are protected with, for example, a silane group such as (Me—O)$_3$-(CH$_2$)$_3$—OH. After the protection step, the silica surface layers at the nanotube mouths are removed to expose fresh silica. The freshly-exposed silica will be reacted with the silane, such as (Me—O)$_3$—Si—(CH$_2$)$_3$—SH to attach the requisite —SH linker to the mouths of the nanotubes.

The length of the alkyl chain in this silane can be varied to allow placement of the —SH linker any desired distance from the nanotube mouth. Three —SH functionalities are then reacted with pyridine disulfide in order to obtain nanotubes with an activated disulfide bond at the nanotube ends.

The surface of the end-cap is then functionalized with the same —SH containing silane used on the mouths of the nanotubes. Hence, nanotubes with an activated disulfide at their mouths and end-caps with an —SH group on their surface are available for linkage through disulfide bond formation.

Other types of covalent bonds, for example amide and ester bonds, can be used to attach an end-cap to the nanotube. Siloxane based linking can also be used. This would be particularly useful when the cap is composed of silica as the silanol sites on the silica surface reacts spontaneously with siloxanes to form a covalent oxygen-silicon bond. For metal based nanotubes or end-caps, thiol linkers can be used for attachment. For example, molecule $(Me-O)_3-Si-(CH_2)_3-SH$ could be attached to a silica nanotube and a gold nanoparticle attached as the end-cap using the —SH end of this molecule. It is well known that such thiols form spontaneous As—S bonds with gold surfaces.

Contemplated end-caps for the invention include nanoparticles that can be electrophoretically placed within the mouths of nanotubes so that the entire mouth of the nanotube is blocked when disulfide bonds are formed between the nanotube and the nanoparticle as described in Miller, S. A. and C. R. Martin, "Electroosmotic Flow in Carbon Nanotube Membranes," *J. Am. Chem. Soc.*, 123(49):12335–12342 (2001).

The end-cap ("or nanocap") can be used to impart several novel functions and degrees of intelligence to the nanotube-nanocap delivery system. These include the sealing of the payload contents (such as the surrogate marker) within the nanotube in a cost-effective manner.

The nanocap can also provide a mechanism whereby the nanotube payload contents can be selectively released. For example, when used for the in-vivo delivery of a surrogate marker, the nanotube can be designed to release its payload either at the surface of the target cell or within its cytoplasm. This may be achieved by sensing a chemical, physical or biological signal present in the local environment. Alternatively, a remote external energy source, such as ultrasonic irradiation, can be used to selectively release the payload from the nanotube. Time-controlled degradation of the biomaterials used to construct the nanotube and/or nonocaps can also provide a release mechanism.

For example, a nanotube containing membrane is mounted in a U-tube cell with Platinum electrodes immersed into the buffer solution on either side of the membrane. The —SH-functionalized end-caps are added to the cathode half-cell. The buffer solution is maintained at pH=7 so that a small fraction of the —SH groups on the end-caps are deprotonated. These negatively charged particles are driven into the mouths of the nanotubes electrophoretically by using the Platinum electrodes to pass a constant current through the membrane. Hence, the electrophoretic force causes the end-caps to nestle into the nanotube mouths, where disulfide bond formation will occur.

As an alternative to the electrophoretic assembly method, —SH labeled end-caps can be suspended in solution together with the activated disulfide labeled nanotubes. Here, the nanoparticle caps can spontaneously self-assemble to the nanotubes. The self-assembly of gold nanospheres and latex particles to template prepared polymeric and metal nanowires is described by Sapp, S. A. et al., "Using Template-Synthesized Micro- and Nanowires as Building Blocks for Self-Assembly of Supramolecular Architectures," *Chem. Mater.*, 11:1183–1185 (1999).

In addition to —SH linking, other covalent linking methods can be used to link nanotubes and end-caps. Non-covalent linking methods can be used. These include, for example, DNA hybridization (Mirkin, C. A., "Programming the Self-Assembly of Two and Three-Dimensional Architectures with DNA and Nanoscale Inorganic Building Blocks," *Inorg. Chem.*, 39:2258–2272 (2000)), the biotin/avidin interaction (Connolly, S. and D. Fitzmaurice, "Programmed Assembly of Gold Nanocrystals in Aqueous Solution," *Adv. Mater.*, 11:1202–1205 (1999)), and antigen/antibody interactions (Shenton, W. et al., "Directed Self-Assembly of Nanoparticles into Macroscopic Materials Using Antibody-Antigen Recognition," *Adv. Mater.*, 11:449 (1999)).

Preferred nanotubes are those comprising silica or polymers. Silica nanotubes can be prepared using sol-gel template synthesis, as described in Lakshmi, B. B. et al., "Sol-Gel Template Synthesis of Semiconductor Oxide Micro- and Nanostructures," *Chem. Mater.*, 9:2544–2550 (1997); Lakshmi, B. B. et al., "Sol-Gel Template Synthesis of Semiconductor Nanostructures," *Chem. Mater.*, 9:857–862 (1997). The template membrane is immersed into a standard tetraethylorthosilicate sol so that the sol fills the pores. After the desired emersion time, the membrane is removed, dried in air, and then cured at 150° C. This yields silica nanotubes lining the pore walls of the membrane plus silica surface films on both faces of the membrane. The surface films are removed by briefly polishing with slurry of alumina particles. The nanotubes are then liberated by dissolving the template membrane and collected by filtration.

The outside diameter of the nanotube can be controlled by varying the pore diameter of the template membrane, the length of the nanotube can be controlled by varying the thickness of the template membranes, and the inside diameter of the nanotube can be controlled by varying the immersion time in the sol.

Polymer nanotubes can be prepared from many substances that are composed of monomer units. "Monomer units," as used herein, refers to the individual moieties that are repeated to form "polymers." Multiple monomer units are covalently attached when tin the form of a backbone of a polymer. Polymers that are made from at least two different types of monomer units are referred to as "copolymers." Polymerizing or copolymerizing describes the process by which multiple monomers are reacted to form covalently linked monomer units that form polymers or copolymers, respectively. A discussion of polymers, monomer units, and the monomers from which they are made may be found in Stevens, *Polymer Chemistry: An Invasion;* $3^{rd}$ ed., Oxford University Press (1999).

Polymeric nanotubes can be prepared using a solution deposition method as described in Depak, V. M. and C. R. Martin, "Preparation of Polymeric Micro- and Nanostructures Using a Template-Based Deposition Method," *Chem. Mater.*, 11:1363–1367 (1999). This method entails depositing a solution of the desired polymer within the pores of the template membrane and allowing the solvent to evaporate. In addition, polymer nanotubes can be prepared by polymerizing a monomer within the pore as described by Martin, C. R., "Template Synthesis of Electronically Conductive Polymer Nanostructures," *Acc. Chem. Res.*, 28:61–68 (1995).

Preferred polymers include polystyrene, polyorganosiloxane, poly(methyl methacrylate), polystyrene, polylactic acids, and other biodegradable polymers, acrylic latexes, polyorganosilioxane, cellulose polyethylene, poly(vinyl chloride), poly(ethyl methacrylate), poly(tetrafluoroethylene), poly(4-iodostyrene/divinyl/benzene), poly(4-vinylpyridine/vidinylbenzene), poly(styrene/divinyl benzene), crosslinked melamine particles, phenolic polymer colloids, polyamide 6/6, natural rubber, naturally occurring biopolymers such a salgenates, and collagen, or mixtures thereof.

Functionalization of Nanoparticle Surface

Methods used to functionalize a nanoparticle surface, in accordance with the present invention, depend on the composition of the nanoparticle and are well known in the art. For example, functionalization of silica nanoparticles is accomplished using silane chemistry. The detecting means and/or the surrogate marker can be attached to the surfaces of the nanoparticle by attaching them to the surface of the nanoparticle while the nanoparticle is still embedded with a template. Alternatively, while the nanoparticle is embedded in the templates, a hydrolytically unstable silane is reacted with surface silanol sites on nanoparticle to obtain covalent oxygen/silicon bonds between the surface and the silane. Either the detecting means and/or the surrogate marker can then be attached to the surface of the nanoparticle after dissolution of the template.

The surface of polymer-based nanoparticles can also be functionalized using well-known chemical methods. For example, the methods employed for polylactide synthesis allow for differential end-functionalization. Polymerization occurs by an insertion mechanism mediated by Lewis acids such as $Sn^{2+}$ whose bonds with oxygen have significant covalent character. An alcohol complexed with the metal ion initiates polymerization, which continues by stepswise ring-opening of the lactide monomers to generate a new alkoxide-metal complex capable of chain growth. The polymer molecular weight can be controlled by the molar ratio of initiating alcohol to the lactide monomer. The resulting polyester possesses directly with a hydroxyl terminus (from the first monomer) and either a detecting means and/or surrogate marker at the ester terminus determined by the structure of the initiating alcohol. The latter can contain a variety of detecting means and/or surrogate markers.

Additionally, the detecting means and/or surrogate marker can be introduced by copolymerization. Naturally amino acids re sterically similar to lactic acid but offer a variety of functional groups on their side-chains (—OH, —$CO_2H$, —$NH_2$, —SH, etc.) Monomer derived from an amino acid and lactic acid can be synthesized by standard methods and used for random copolymerization with lactide.

By functionalizing the nanoparticle with either a detecting means and/or surrogate marker, the present invention provides nanostructure-based assemblies that can immobolize a specific protein or cell. See Langer, R., "Tissue Engineering," *Mol. Ther.*, 1:12–15 (2000). Detecting means, for example proteins, including antibodies or peptides, RNA, or DNA, aptamers, cellular receptor ligands, are attached to the nanoparticle surface. Such detecting means may be attached covalently, including attachment via functional groups introduced by the functionalization of the surface. Alternatively, the detecting means may be covalently attached via linker molecules. Non-covalent linkages can also be used to attach detecting means and/or surrogate markers to the nanoparticle. Examples of non-covalent linkages include, and are not limited, absorption via hydrophobic binding or Van der Waals forces, hydrogen bonding, acid/base interactions, and electrostatic forces.

For nanoparticles comprising a hollow void in which the surrogate marker can be contained, a surrogate marker can be loaded into the void using an electrophoretic force. (See Miller, S. A. and C. R. Martin, "Electroosmotic Flow in Carbon Nanotube Membranes," *J. Am. Chem. Soc.*, 123(49): 12335–12342 (2001)). Alternatively, nanoparticles embedded within the synthesis membrane can be filled with a surrogate marker by vacuum filtering a solution containing the surrogate marker through the synthesis membrane. (See Parthasarathy, R. and C. R. Martin, *Nature*, 369:298 (1994)). For nanoparticles prepared by formation within an alumina template film prior to removal of the alumina from the underlying aluminum surface, they can be filled by simply applying a solution containing the surrogate marker to the surface of the film (where the opening to the hollow void is located) and allowing the solvent to evaporate. Multiple applications can be used, if needed.

Means for Detecting Target Analytes/Biomarkers

The present invention contemplates using known bifunctional or hybrid molecules for detecting target analytes/biomakers. Some of these molecules include, but are not limited to, chimeric antibodies; bispecific antibodies (i.e., antibodies produced through enzymatic digestion of parent antibodies and controlled reconstitution using Fab fragments obtained from two different parents); conventional immunoconjugates, which can include an imaging agent covalently attached or chelated to an antibody or antibody fragment through established immunochemical methods; and fusion proteins, generated from hybrid genes developed and expressed through recombinant methods.

According to the present invention, other contemplated means for detecting a target analyte/biomarker include antibodies, antigens, haptens and nucleic acid probes with site-directed effectors (i.e., fluorophores). DNA, including branched DNA, can also be used in accordance with the present invention as a means for detecting target analytes/biomarkers. For example, it has been shown that particular proteins recognize and bind to specific sites on the DNA. See Seeman, *Clin. Chem.*, 39:722 (1993).

The present invention preferably utilizes aptamers to non-invasively detect drugs, biomarkers, and other analytes in exhaled breath and other bodily fluids, such as blood. In a preferred embodiment, the invention includes aptamers in combination with nanotechnology (i.e., nanotubes) to provide an effective method for signaling the presence of a target analyte/biomarker in bodily fluids, particularly in blood.

The discover of the SELEX™ (Systematic Evolution of Ligands of EXponential enrichment) methodology enabled the identification of aptamers that recognize molecules other than nucleic acids with high affinity and specificity (Ellington and Szostak, "In vitro selection of RNA molecules that bind specific ligands," *Nature*, 346:818–822 (1990); Gold et al., "Discovery of oligonucleotide functions," *Ann. Rev. Biochem.*, 64:763–797 (1995); Tuerk and Gold, "Systematic evolution of ligands by exponential enrichment—RNA ligands to bacteriophage-T4 DNA-polymerase," *Science*, 249:505–510 (1990)). Aptamers have been selected to recognize a broad range of targets, including small organic molecules as well as large proteins (Gold et al., supra.; Osborne and Ellington, "Nucleic acid selection an the challenge of combinatorial chemistry," *Chem. Rev.*, 97:349–370 (1997)).

The aptamers derived from the SELEX methodology may be utilized in the present invention. The SELEX methodology enables the production of aptamers, each of which have a unique sequence and the property of binding specifically to a desired target compound or molecule. The SELEX methodology is based on the insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. See also Jayasena, S., "Aptamers: An Engineering Class of Molecules That Rival Antibodies for Diagnostics," *Clinical Chemistry*, 45:9, 1628–1650 (1999).

Aptamers that can be used in the present invention include those described in U.S. Pat. No. 5,656,739 (hereinafter the '739 patent), which discloses the advantages of synthetic oligonucleotides as assembly templates. The '739 patent describes nucleic acids as particularly useful assembly templates because they can be selected to specifically bind nonoligonucleotide target molecules with high affinity (e.g.; Tuerk and Gold (1990), supra), and because they can hybridize by complementary base pairing. Both forms of recognition can be programmably synthesized in a single molecule or hybridized into a single discrete structure.

As described herein, nanoparticles can be prepared with hollow interiors and include functionalized end-caps with detecting means. A variety of methods are available to functionalize an end-cap, depending on the composition of the end-cap. For example, an end-cap can be functionalized using well-known chemical methods such as those employed for polylactide synthesis. Detecting means (i.e., aptamers, proteins, antibodies) can be introduced to "functionalized" end-caps by copolymerization. For example, monomers derived from an amino acid or lactic acid can be synthesized using standard methods and then used for random copolymerization with lactic. Such functionalized end-caps can allow for the application of the detecting means to the end-cap.

In one embodiment, the detecting means are aptamers that can be attached to proteins utilizing methods well known in the art (see Brody, E. N. and L. Gold, "Aptamers as therapeutics and diagnostics agents," *J. Biotechnol.* 74(1): 5–13 (2000) and Brody, E. N. et al., "The use of aptamers in large arrays for molecular diagnostics," *Mol Diagn.*, 4(4):381–8 (1999)). For example, photo-cross-linkable aptamers allow for the covalent attachment of aptamers to proteins. Such aptamer-linked proteins can then be immobilized on a functionalized end-cap of a nanoparticle. For example, aptamer-linked proteins can be attached covalently to a nanoparticle end-cap, including attachment of the aptamer-linked protein by functionalization of the end-cap surface. Alternatively, aptamer-linked proteins can be covalently attached to an end-cap via linker molecules. Non-covalent linkage provides another method for introducing aptamer-linked proteins to an end-cap. For example, an aptamer-linked protein may be attached to an end-cap by absorption via hydrophilic binding or Van der Waals forces, hydrogen bonding, acid/base interactions, and electrostatic forces.

Aptamer-end-caps, according to the present invention, are bound to the nanoparticle until the detection of a target analyte/biomarker by the aptamer. End-caps are attached to nanoparticles using a variety of methods. Methods for attaching an end-cap to a nanoparticle include, but are not limited to, using: electrostatic attraction, hydrogen bonding, acid and/or basic sites located on the end-cap/nanoparticle, covalent bonds, and other chemical linkages.

Sensor Technology

Sensor technology is used by the present invention to detect the presence of a surrogate marker released from a nanoparticle-based sensor in a bodily fluid sample. The surrogate marker signifies the presence and quantity of a target analyte/biomarker. The present invention contemplates using sensor technology based on surface acoustic wave (SAW) sensors. These sensors oscillate at high frequencies and respond to perturbations proportional to the mass load of certain molecules. This occurs in the vapor phase on the sensor surface. The resulting frequency shift is detected and measured by a computer. Usually, an array of sensors (4–6) is used, each coated with a different chemoselective polymer that selectively binds and/or absorbs vapors of specific class of molecules. The resulting array, or "signature" identifies specific compounds. Sensitivity of the arrays is dependent upon the homogeneity and thickness of the polymer coating.

Surface-acoustic wave (SAW) gas-sensors generally include a substrate with piezoelectric characteristics covered by a polymer coating, which is able to selectively absorb the target surrogate markers. The variation of the resulting mass leads to a variation of its resonance frequency. This type of sensor provides very good mass-volume measures of the surrogate markers. In the SAW devices, the surrogate marker is used to propagate a surface acoustic wave between sets of interdigitated electrodes. The chemoselective material is coated on the surface of the transducer. When a surrogate marker interacts with the chemoselective material coated on the substrate, the interaction results in a change in the SAW properties, such as the amplitude or velocity of the propagated wave. The detectable change in the characteristics of the wave indicates the presence and concentration of the surrogate marker (and corresponding target analyte/biomarker).

Certain embodiments use known SAW devices described in numerous patents and publications, including U.S. Pat. Nos. 4,312,228 and 4,895,017, and Groves W. A. et al., "Analyzing organic vapors in exhaled breath using surface acoustic wave sensor array with preconcentration: Selection and characterization of the preconcentrator adsorbent," *Analytica Chimica Acta*, 371:131–143 (1988).

Other types of chemical sensors known in the art that use chemoselective coating applicable to the operation of the present invention include bulk acoustic wave (BAW) devices, plate acoustic wave devices, interdigitated microelectrode (IME) devices, optical waveguide (OW) devices, electrochemical sensors, and electrically conducting sensors.

In another embodiment, the invention uses fluid sensor technology, such as commercial devices known as "artificial noses," "electronic noses," or "electronic tongues." These devices are capable of qualitative and/or quantitative analysis of simple or complex gases, vapors, odors, liquids, or solutions. A number of patents and patent applications which describe fluid sensor technology include the following: U.S. Pat. Nos. 5,945,069; 5,918,257; 5,891,398; 5,830,412; 5,783,154; 5,756,879; 5,605,612; 5,252,292; 5,145,645; 5,071,770; 5,034,192; 4,938,928; and 4,992,244; and U.S. patent application Ser. No. 2001/0050288. Certain sensitive, commercial off-the-shelf electronic noses, such as those provided by Cyrano Sciences, Inc. ("CSI") (i.e., CSI's portable Electronic Nose and CSI's Nose-Chip™ integrated circuit for odor-sensing—U.S. Pat. No. 5,945,069), can be used in the present invention to detect the presence of surrogate markers in bodily fluid samples.

Other embodiments of the present invention use sensor technology selected from semiconductive gas sensors; mass spectrometers; and IR, UV, visible, or fluorescence spectrophotometers. With these sensors, a surrogate marker changes the electrical properties of the semiconductors by making their electrical resistance vary, and the measurement of these alternatives allows the determination of the concentration of surrogate markers present in the sample. The methods and apparatus used for detecting surrogate markers generally have a brief detection time of a few seconds.

Additional recent sensor technologies included in the present invention include apparatus having conductive-polymer gas-sensors ("polymeric"), aptamer biosensors, and amplifying fluorescent polymer (AFP) sensors.

Conductive-polymer gas-sensors (also referred to as "chemoresistors") are coated with a film sensitive to the molecules of certain surrogate markers. On contact with the molecules, the electric resistance of the sensors change and the measurement of the variation of this resistance enable the concentration of the sensors surrogate substance (and corresponding target analyte/biomarker) to be determined. An advantage of this type of sensor is that it functions at temperatures close to ambient. Different sensitivities for detecting different surrogate markers can be obtained by modifying or choosing an alternate conductive polymer.

Polymeric gas sensors can be built into an array of sensors, where each sensor responds to different gases and augment the selectivity of the surrogate marker.

Aptamer biosensors can be utilized in the present invention for detecting the presence of surrogate markers in bodily fluid samples. Aptamer biosensors are resonant oscillating quartz sensors that can detect minute changes in resonance frequencies due to modulations of mass of the oscillating system, which results from a binding or dissociation event.

Similarly, amplifying fluorescent polymer (AFP) sensors may be utilized in the present invention for detecting the presence of surrogate markers in bodily fluid samples. AFP sensors are extremely sensitive and highly selective chemosensors that use amplifying fluorescent polymers. When vapors bind to thin films of the polymers, the fluorescence of the film decreases. A single molecule binding event quenches the fluorescence of many polymer repeat units, resulting in an amplification of the quenching. The binding of surrogate markers to the film is reversible, therefore the films can be reused.

The results from the sensor technology analysis of the bodily fluid samples are optionally provided to the user (or patient) via a reporting means. In one embodiment, the sensor technology includes the reporting means. Contemplated reporting means include a computer processor linked to the sensor technology in which electronic or printed results are provided. Alternatively, the reporting means can include a digital display panel, transportable read/write magnetic media such as computer disks and tapes which can be transported to and read on another machine, and printers such as thermal, laser or ink-jet printers for the production of a printed report. The reporting means can provide the results to the user (or patient) via facsimile, electronic mail, mail or courier service, or any other means of safely and securely sending the report to the patient. Interactive reporting means are also contemplated by the present invention, such as an interactive voice response system, interactive computer-based reporting system, interactive telephone touch-tone system, or other similar system. The report provided to the user (or patient) may take many forms, including a summary of analyses performed over a particular period of time or detailed information regarding a particular bodily fluid sample analysis. Results may also be used to populate a financial database for billing the patient, or for populating a laboratory database or a statistical database.

Specific conditions/diseases that can be detected using the present invention are listed in *Merck Manual Diagnosis and Therapy*, $17^{th}$ ed., Merck & Company, Inc., 1999, which include, but are not limited to, blood disorders (i.e., blood coagulation disorders, lymphedema, hemochromatosis, leukemia, lymphedema, myelodysplastic syndromes, neutropenia), cancers (i.e., brain tumors, breast cancer, colorectal cancer, lymphomas, lung cancer, prostate cancer), cardiovascular disorders (i.e., coronary artery disease, congenital heart disease, atherosclerosis, aneurysm, peripheral arterial disease), disorders of the esophagus (i.e., achalasia), Barrett's esophagus), intestinal disorders (i.e., Celiac disease, Crohn's disease, inflammatory bowel disease), liver diseases and disorders (i.e., cirrhosis of the liver, hepatitis, Wilson's disease), pancreatic diseases and disorders (i.e., pancreatitis, cystic fibrosis), disorders of the ear, nose or throat (i.e., Meniere's disease, strep throat), endocrine disorders (i.e., congenital adrenal hyperplasia, diabetes, hypoglycemia, hyperparathyroidism, hypoparathyroidism, and Cushing's syndrome), eye disorders (i.e., retinoblastoma, uveitis, Lebers optic neuropathy, keratoconus), genetic disorders (i.e., Marfan's syndrome, porphyries, Huntingdon's disease, normal pressure hydrocephalus (NPH), Wilson's disease), gynecologic disorders (i.e., polycystic ovarian syndrome, endometriosis), immune disorders (i.e., AIDS, Addison's disease, Lupus, Sjogren's syndrome), infectious diseases (i.e., bacterial (rickettsial diseases, anthrax, endocarditis, salmonellosis), viral (chickenpox, herpes, influenza, pneumonia, shingles, West Nile virus), fungal (aspergillosis), parasitic (malaria, scabies, pinworms), prion (Creutzfeldt Jakob Disease)), metabolism disorders (fatty oxidation disorders, glycogen storage disorders I and II, glutaric acidemia), musculkoskeletal disorders (osteoporosis), neurological disorders (Alzheimer's disease, meningitis, demyelinating diseases), respiratory conditions, and urological disorders (hemolytic uremic syndrome, urinary tract infections).

EXAMPLE 1

Diagnosis of Traumatic Brain Injury (TBI)

The present invention provides methods for diagnosing acute and/or chronic neurological diseases and disorders (i.e., Alzheimer's disease, Parkinson's disease) and other clinical conditions by detecting in vitro analytes/biomarkers of oxidative stress. For example, it is known that certain αII-spectrin breakdown products, including isoprostane, levels increase in cerebral spinal fluid and blood after traumatic brain injury.

In accordance with the present invention, nanostructure-based assemblies are created in which the detecting means is designed to specifically detect and localize the assembly to isoprostanes and/or αII-spectrin breakdown products. In a preferred embodiment, the detecting means is an aptamer designed to bind to isoprostanes and/or αII-spectrin breakdown products. A sample of a patient's bodily fluid (i.e., blood or cerebral spinal fluid) is placed into a sealed vial containing the nanostructure-based assemblies designed as described above.

In one embodiment, the sample is incubated at an elevated temperature to allow any surrogate markers that were released from the nanostructure-based assemblies to diffuse out of the liquid phase into the "headspace" (gas phase) within the sealed vial. Under constant conditions of temperature, pressure, and equilibration time, the vapor phase in the sample vial is sampled and separated on a suitable gas chromatographic column. The surrogate markers are detected using flame ionization detector or nitrogen phosphorous detector.

In another embodiment, an "electronic nose" is used to detect and measure the amount of surrogate marker released in the sample via to assess whether the patient suffers from traumatic brain injury. As contemplated by the subject invention, the electronic nose can include the following components: (a) a sensor having an array of polymers capable of detecting the presence of the surrogate marker in the headspace of the vial, wherein the sensor responds to the surrogate marker by changing the resistance in each polymer resulting in a pattern change in the sensor array; (b) a processor for receiving the change in resistance, comparing the change in resistance with a previously measured change in resistance, and identifying the presence of the surrogate marker from the pattern change, and (if requested) the concentration of the surrogate marker from the amplitude. In a related embodiment, the sensor can include measuring circuitry and an output device can be included (i.e., screen display, audible output, printer). The processor can include a neural network for comparing the change in resistance with a previously measured change in resistance to find a best match.

By measuring isoprostane level and/or αII-spectrin breakdown products using the nanostructure-based assemblies of the invention, a clinician can not only identify if a patient is suffering from TBI, but once diagnosed, a clinician can follow the course of the brain injury. Moreover, by continuously testing samples of bodily fluid in accordance with the present invention, it is possible to evaluate th the efficacy of interventions in real-time for treating TBI. Accordingly, the method of the present invention can also evaluate pharmacodynamics and pharmacokinetics for drug interventions in individuals.

EXAMPLE 2

Diagnosis of Bronchogenic Carcinoma

In an embodiment, a nanostructure-based assembly of the present invention can be designed to detect bronchogenic carcioma. Bronchogenic carbinomas produce carcinoma metabolites that cause the occurrence of O-toluidine in exhaled breath. The detecting means of the nanostructure-based assembly can be in the form of an aptamer. Using routine techniques, the aptamer can be designed so that it is specific for O-toluidine (O-toluidine-aptamer). The O-toluidine-aptamer can be linked to a nanoparticle using functionalization methods as described above. The nanoparticle contains a surrogate marker that would be released in the presence of O-toluidene. Upon exposing the nanostructure-based assembly to a sample of bodily fluid (i.e., exhaled breath) suspected of containing O-toluidine, the O-toluidine-aptamer specifically binds to any O-toluidine present in the sample and causes the release of the surrogate marker to generate a signal that O-toluidine is present in the bodily fluid sample.

In one embodiment, sensor technology used to detect the surrogate marker in the sample has the following components: (a) a surface-acoustic wave sensor capable of detecting the presence of the surrogate marker in the mixture of bodily fluid (i.e., expired breath) and the nanostructure-based assembly, wherein the sensor responds to the surrogate marker by a shift in the resonant frequency; (b) an oscillator circuit having the sensor as an active feedback element; (c) a frequency counter in communication with the oscillator circuit to measure oscillation frequency which corresponds to resonant frequency of the sensor; and (d) a processor for comparing the oscillation frequency with a previously measured oscillation frequency with a previously measured oscillation frequency of the surrogate marker and determining presence and concentration of the surrogate marker therefrom. The sensor technology of the present invention an include measuring circuitry and an output device (i.e., screen display, audible output, and printer).

The processor can include a neural network (not shown) for pattern recognition. Artificial Neural Networks (ANNs) are well understood by the skilled artisan. ANNS are self-learning; the more data presented, the more discriminating the instrument becomes. By running many standard samples of bodily fluids and storing the results in computer memory, the application of ANN enables the sensor technology to "understand" the significance of the sensor array outputs better and to use this information for future analysis, "Learning" is achieved by varying the emphasis, or weight, that is placed on the output of one sensor versus another. The learning process is based on the mathematical, or "Euclidean," distance between data sets. Large Euclidean distances represent significant differences in sample-to-sample surrogate marker characteristics.

Thus, a time- and cost-efficient test for the presence of bronchogenic carcinoma is provided.

EXAMPLE 3

Diagnosis of Prostate Cancer

In another embodiment, a detecting means is designed for a biomarker of a specific cancer, i.e., prostate cancer. Prostate cancers produce a protein, prostate specific antigen (PSA). In a preferred embodiment, the detecting means is an aptamer designed to specifically bind to PSA (PSA-aptamer). The PSA-aptamer can be attached to a nanoparticle using functionalization methods as described above. The nanoparticle also includes a surrogate marker that is released in the presence of PSA. In one embodiment, the PSA-aptamer and the surrogate marker are attached to the surface of the nanoparticles using functionalized methods as described above. The nanostructure-based assembly is introduced to a sample of bodily fluid (i.e., blood) to identify the presence of PSA. Where PSA is present in the bodily fluid sample, the PSA-aptamer will bind to PSA and affect the release of the surrogate marker form the nanoparticle to signal the presence and concentration of PSA in the bodily fluid sample.

In a preferred embodiment, the nanostructure-based assembly is composed of a hollow nanoparticle. The detecting means, i.e., PSA-apatamer, is attached to an end-cap that fits onto an opening of a nanoparticle. The nanoparticle preferably encapsulates a surrogate marker. IN a rapid test for the presence of prostate cancer, or a recurrence of prostate cancer, the PSA-nanostructure-based assembly is mixed with a sample of bodily fluid (i.e., exhaled breath, exhaled condensates with proteins). The surrogate marker is released from the nanoparticle after PSA (the biomarker of interest) interacts with the PSA-aptamer and "uncaps" the nanoparticle. Using any of a number of previously disclosed sensor technologies, the surrogate marker is detected in the sample of exhaled breath to indicate the presence and/or concentration of PSA in the sample.

In a related embodiment, the sensor technology used to detect any surrogate markers in the sample of bodily fluids (i.e., exhaled breath or exhaled condensates with proteins) comprises at least one polymer (or an array of polymers) exposed to the sample-nanoparticle mixture. Thus, a variety of nanostructure-based assemblies can be applied to a sample of bodily fluid to detect more than one target analyte/biomarker. Each of the individual polymers of the sensor technology swells differently in the presence of a specific surrogate marker, creating a change in the resistance of the membrane and generating an analog voltage in response to the specific surrogate marker ("signature"). Based on the pattern change in the sensor array, the normalized change in resistance is then transmitted to a processor to identify the type and quantity of the surrogate marker. The unique response results in a distinct electrical fingerprint characterizing the substance. The pattern of resistance changes of the array indicates the presence of a specific surrogate marker and the amplitude of the pattern indicates its concentration.

In another embodiment, the sensor technology can be designed so that patients provide a sample of bodily fluid (i.e., exhaled breath or exhaled condensates with proteins) directly into the device. For example, a mouthpiece or nosepiece is provided for interfacing a patient with the sensor technology to readily transmit a sample of exhaled breath to the sensor technology to be mixed with nanostructure-based assemblies. This, however, is not a limitation on the invention as samples of bodily fluids can be sampled immediately or stored.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for detecting ex vivo a target analyte/biomarker comprising:
   (a) collecting a sample of bodily fluid in a container, wherein the sealed container comprises the sample of bodily fluid and a headspace;
   (b) mixing ex vivo to the bodily fluid in the container a nanostructure-based assembly that comprises a surrogate marker where the surrogate marker is released from the nanostructure-based assembly in the presence of a target analyte/biomarker;
   (c) applying sensor technology to the headspace or bodily fluid sample in the container, which contains the mixture of nanostructure-based assembly and bodily fluid sample in the container, wherein the sensor technology detects a surrogate marker released from the nanostructure-based assembly in the sealed container; and
   (d) determining whether the sample contains the target analyte/biomarker by using the sensor technology to detect the presence of the surrogate marker, wherein the detection of the surrogate marker indicates the presence of the target analyte/biomarker in the sample of bodily fluid in the container.

2. The method according to claim 1, wherein the nanostructure-based assembly comprises at least one nanotube comprising a hollow interior, a first end, a second end, surrogate marker located within the hollow interior, and an end-cap, wherein the first end is open and the second end is closed, the first end being blocked with the end-cap to prevent the release of the surrogate marker, wherein a means for detecting the target analyte/biomarker is attached to the end-cap; wherein the means for detecting the target analyte/biomarker can bind to the target analyte/biomarker; and wherein when the means for detecting the target analyte/biomarker binds to the target analyte/biomarker, the end-cap is displaced from the first end to release the surrogate marker.

3. The method according to claim 2, wherein the means for detecting to the target analyte/biomarker is selected from the group consisting of aptamers, antibodies, proteins, and receptor ligands.

4. The method according to claim 3, wherein the aptamer is capable of binding to the target analyte/biomarker selected from the group consisting of $\alpha$II-spectrin breakdown products and protease-specific spectrin breakdown products.

5. The method according to claim 1, wherein the target analyte/biomarker is a nucleic acid, a protein, an illicit drug, an explosive, a toxin, a pharmaceutical, a carcinogen, a poison, an allergen, or an infectious agent.

6. The method according to claim 1, wherein the target analyte/biomarker is selected from the group consisting of acetaldehyde, acetone, ammonia, CO, chloroform, dichlorobenzene, diethylamine, hydrogen, isoprene, methanethiol, methylethylketone, O-toluidine, pentane sulfides and sulfides, $H_2S$, MES, and $Me_2S$.

7. The method according to claim 1, wherein the bodily fluid sample is selected from the group consisting of: exhaled breath, blood, urine, bile, sweat, feces, semen, saliva, mucus, and cerebral spinal fluid.

8. The method according to claim 1, wherein the sensor technology is selected from the group consisting of surface-acoustic-wave sensors; fluid sensor technology; semiconductive gas sensors, mass spectrometers; IR, UV, visible and fluorescence spectrophotometers; conductive-polymer gas-sensors; aptamer biosensors; and amplifying fluorescent polymer sensors.

9. The method according to claim 1, wherein the sensor technology comprises:
   (a) a surface-acoustic wave (SAW) sensor capable of detecting the presence of a surrogate marker in a sample of bodily fluid, wherein the SAW sensor responds to the surrogate marker by a shift in the resonant frequency;
   (b) an oscillation circuit having the SAW sensor as an active feedback element;
   (c) a frequency counter in communication with said oscillator circuit to measure oscillation frequency which corresponds to resonant frequency of the SAW sensor; and
   (d) a processor for comparing the oscillation frequency with a previously measured oscillation frequency of the surrogate marker and determining presence and concentration of the surrogate marker therefrom.

10. The method according to claim 1, wherein the sensor technology comprises:
   (a) a sensor having an array of polymers capable of detecting the presence of the surrogate marker in the sample of bodily fluid, wherein said sensor responds to the surrogate marker by changing the resistance in each polymer resulting in a pattern change in the sensor array;

(b) a processor for receiving the change in resistance, comparing the change in resistance with a previously measured change in resistance, and identifying the presence of the surrogate marker from the pattern change and the concentration of the surrogate marker from the amplitude.

11. The method according to claim 1, wherein the nanostructure-based assembly comprises at least one nanoparticle comprising a surrogate marker and a means for detecting a target analyte/biomarker, wherein the means for detecting the target analyte/biomarker is bound to the nanoparticle in such a way as to affect the release of the surrogate marker when in the presence of a target analyte/biomarker; wherein when the means for detecting the target analyte/biomarker is in the presence of the target analyte/biomarker, the surrogate marker is released for detection by the sensor technology.

* * * * *

UNITED STATES PATENT AND TRADEMARK OFFICE
CERTIFICATE OF CORRECTION

PATENT NO. : 7,052,854 B2
APPLICATION NO. : 10/678506
DATED : May 30, 2006
INVENTOR(S) : Richard J. Melker et al.

It is certified that error appears in the above-identified patent and that said Letters Patent is hereby corrected as shown below:

Cover Page,
"(75) Inventors: Richard J. Melker, Gainesville, FL (US); Ronald L. Hayes, Gainesville, FL (US); Ka-Wang Kevin Wang, Gainesville, FL (US); Donn Michael Dennis, Gainesville, FL (US)" should read --(75) Inventors: Richard J. Melker, Gainesville, FL (US); Ronald L. Hayes, Gainesville, FL (US); Ka-Wang Kevin Wang, Gainesville, FL (US); Donn Michael Dennis, Gainesville, FL (US); Charles R. Martin, Gainesville, FL (US); Jon D. Stewart, Gainesville, FL (US)--

Cover Page,
Abstract, Line 9, "apparatus" should read --"aptamers"--.

Column 8,
Line 31, "dichlroodiphenyltrichloroethane" should read --dichlorodiphenyltrichloroethane--.

Column 10,
Line 60, "Biophys. .2002" should read --Biophys. J. 2002--.
Line 64, "medium according" should read --medium surrounding--.

Column 11,
Line 24, "nanotubes based" should read --nanotube based--.

Column 13,
Line 33, "(or nanocap")" should read --(or "nanocap")--.

Column 13,
Line 48, "nonocaps" should read --nanocaps--.

Column 14,
Line 54, "Polymer Chemistry: An Invasion" should read --Polymer Chemistry: An Invitation--.

Column 15,
Line 4, "polyorganosilioxane" should read --polyorganosiloxane--.
Line 11, "a salgenates" should read --as algenates--.
Line 23, "in the templates" should read --in the template--.

Column 16,
Line 58, "Discovery of" should read --Diversity of--.

UNITED STATES PATENT AND TRADEMARK OFFICE
CERTIFICATE OF CORRECTION

PATENT NO. : 7,052,854 B2
APPLICATION NO. : 10/678506
DATED : May 30, 2006
INVENTOR(S) : Richard J. Melker et al.

It is certified that error appears in the above-identified patent and that said Letters Patent is hereby corrected as shown below:

Column 20,
Line 40, "musculkoskeletal disorders" should read --musculoskeletal disorders--.

Column 21,
Line 13, "the sample via to" should read --the sample vial to--.
Line 50, "Bronchogenic carbinomas" should read --Bronchogenic carcinomas--.

Column 22,
Line 15, "invention an include" should read --invention can include--.
Line 61, "IN a rapid test" should read --In a rapid test--.

Signed and Sealed this

Twenty-eighth Day of November, 2006

JON W. DUDAS
*Director of the United States Patent and Trademark Office*